United States Patent
Mellies

(10) Patent No.: US 8,216,592 B2
(45) Date of Patent: Jul. 10, 2012

(54) INFECTION MODEL FOR DEVELOPING CHEMOTHERAPEUTIC AGENTS

(75) Inventor: Jay L. Mellies, Portland, OR (US)

(73) Assignee: The Reed Institute, Portland, OR (US)

( * ) Notice: Subject to any disclaimer, the term of this patent is extended or adjusted under 35 U.S.C. 154(b) by 60 days.

(21) Appl. No.: 12/297,430

(22) PCT Filed: Apr. 19, 2007

(86) PCT No.: PCT/US2007/009561
§ 371 (c)(1),
(2), (4) Date: Feb. 9, 2009

(87) PCT Pub. No.: WO2007/123992
PCT Pub. Date: Nov. 1, 2007

(65) Prior Publication Data
US 2009/0297451 A1    Dec. 3, 2009

(51) Int. Cl.
*A61K 39/00* (2006.01)
*A61K 38/28* (2006.01)
*A01N 63/00* (2006.01)
*C07G 11/00* (2006.01)

(52) U.S. Cl. ............ 424/265.1; 424/93.4; 514/4.6; 536/16.8

(58) Field of Classification Search ......... 424/265.1, 424/93.4; 514/4.6; 536/16.8
See application file for complete search history.

(56) References Cited

U.S. PATENT DOCUMENTS

| 5,549,889 A | 8/1996 | Zuckerman et al. |
| 6,479,055 B1 | 11/2002 | Bolognesi et al. |
| 6,905,670 B2 * | 6/2005 | Ausubel et al. ............... 506/10 |
| 7,326,528 B2 | 2/2008 | Chow et al. |
| 2002/0194624 A1 * | 12/2002 | Ausubel et al. |
| 2006/0053497 A1 * | 3/2006 | Ausubel et al. |

OTHER PUBLICATIONS

Notification of Transmittal of the International Search Report and the Written Opinion of the International Searching Authority issued Aug. 1, 2008 in International Application No. PCT/US2007/09561.
Moy, et al. (2006). Identification of Novel Antimicrobials Using a Live-Animal Infection Model, PNAS, Jul. 5, 2006, vol. 103, No. 27, pp. 10414-10419.
Adonizio, et al. (2008). Attenuation of Pseudomonas Aeruginosa Virulence by Medicine Plants in a Caenorhabditis Elegans Model System, Journal of Medical Microbiology (2008), 57, 809-813.
Kurz, et al. (2007). Infection in a Dish: High-Throughput Analyses of Bacterial Pathogenesis, Current Opinion in Microbiology 2007, 10:10-16.

* cited by examiner

*Primary Examiner* — Shin-Lin Chen
(74) *Attorney, Agent, or Firm* — Stoel Rives LLP

(57) ABSTRACT

The present invention relates to a small animal model useful in identifying novel therapies for treating pathogenic diseases. This flexible biotechnology tool is valuable for developing novel chemotherapeutics for a broad range of microbial pathogens.

11 Claims, 4 Drawing Sheets

INFECTION MODEL FOR DEVELOPING CHEMOTHERAPEUTIC AGENTS

FIELD OF THE INVENTION

The present invention relates to an in-vivo animal model useful in identifying novel therapies for treating infectious diseases. In particular, the invention relates to a C. elegans infection model for evaluating the ability of a chemical to disrupt colonization and disease caused by E. coli pathogens.

BACKGROUND

Resistance to chemotherapeutic agents is rendering previously life-saving drugs useless. Perhaps most alarming, multi-drug resistant bacteria are commonplace in hospital settings and lead to untreatable infections. There is a clear need to develop novel, effective therapies against infectious disease. In addition to compounds that kill pathogenic organisms, anti-infectives, or agents that block or disrupt infection, show promise for eliminating disease without killing the organisms.

Anti-infectives are drugs that target the host-microbe interaction, instead of simply targeting the microbe. Anti-infective drugs may enhance and extend the usefulness of the antibiotics currently available by minimizing selective pressure, which leads to resistance. Using small molecules to block bacterial attachment, or to mask host cell receptors specifically utilized by bacterial pathogens without detriment to the host are novel concepts with great promise, potentially revolutionizing how infectious diseases may be treated in the coming century. Exposure to infectious microbes cannot be eliminated, particularly in developing countries and microbes cannot be stopped from evolving resistances to chemical agents. Thus, there is a need to continually evaluate and update the therapeutic arsenal to fight infectious disease and to improve methods for developing combinatorial chemical therapies that target multiple vulnerabilities of the bacterium and minimize microbial resistances.

Therapeutic drug development would benefit from animal infection models that are more flexible than those currently available. Chemical agents that either kill pathogens or halt their growth, traditionally have been identified using in vitro screens. After identification of a candidate compound, animal model systems may then be used to study their effect on the pathogen. There is a continuing need to conduct chemical screens in a convenient, inexpensive in vivo system that will better facilitate testing of novel anti-infective agents and formulating combinatorial therapies.

SUMMARY OF THE INVENTION

In vivo systems for screening and developing chemotherapeutics that disrupt microbial colonization of a host are described herein. The in vivo systems described herein can aid government, academic and biotech researchers in the development of both anti-infectives and drugs that directly target the microbe-host interaction, thereby minimizing the selective pressure that may lead to resistance to traditional chemotherapeutics, such as anti-infectives, antibiotics and antiviral drugs.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
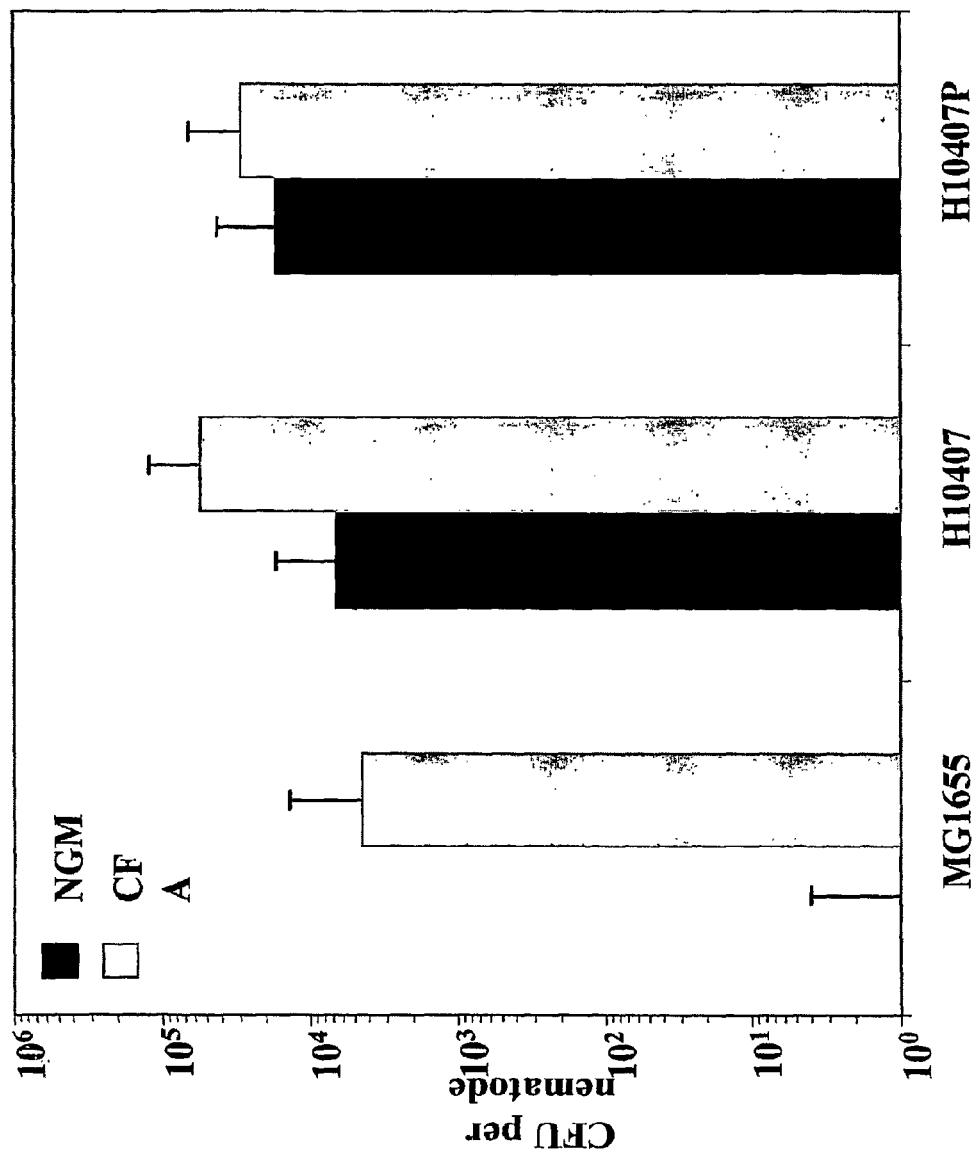
FIG. 1 is a graph demonstrating colonization by ETEC, showing the average colony forming units (CFU) per nematode exposed to the indicated rifampin-resistant bacterial strains on nematode growth medium (NGM) and colonization factor agar (CFA) for 24 hours. Values represent the means of three replicate assays, and error bars indicate 1 standard deviation (SD).

Those skilled in the art will recognize that the systems and methods disclosed can be practiced without one or more of the specific details, or with other methods, components, materials, etc. In some cases, well-known structures, materials, or operations are not shown or described in detail. Furthermore, the described features, structures, or characteristics may be combined in any suitable manner in one or more embodiments. It will also be readily understood that the components of the embodiments as generally described and illustrated in the Figures herein could be arranged and designed in a wide variety of different configurations.

In one embodiment of the present invention, an in vivo system may be used to screen and develop chemotherapeutics that disrupt pathogenic colonization of epithelial cell surfaces. Furthermore, embodiments of the present invention can aid government, academic and biotech researchers in the development of both anti-infectives and drugs that directly target the microbe-host interaction, thereby minimizing the selective pressure that may lead to resistance to traditional antibiotics and other chemotherapeutics.

In one embodiment, a *C. elegans* infection system may be used to screen for potentially therapeutic, chemotherapeutic agents against other pathogenic organisms that can colonize a *C. elegans* host. For example, one embodiment may be used to test the efficacy of a compound against bacterial, viral, and fungal organisms. More particularly, the *C. elegans* host may be infected with enteric bacteria, enteric viruses, and/or yeast and fungal species in order to test the effect of a candidate compound on the organism. Examples of enteric bacterial pathogens may include *Salmonella* spp., *Campylobacter* spp., *E. coli*, *Shigella* spp., *Helicobacter pylori*, *Vibrio* spp., *Clostridium* spp. and others. Examples of enteric viral pathogens can include hepatitis A virus (HAV), Norwalk-like virus (NLV), enterovirus (EV), rotavirus (RV), astrovirus (AV), and others.

In another embodiment, the infection system is amenable to developing specifically designed anti-infective compounds, e.g., chemicals that block and/or disrupt pathogen-host interactions. The *C. elegans* infection system can also be used to evaluate the in vivo activity of compounds that disrupt pathogen virulence gene regulatory processes, directly targeting the pathogen, or to screen libraries of compounds for their ability to limit pathogenic infections. Additionally, drug development and screening can be performed using wild type pathogens, making drug discovery more robust from the very beginning of the process. Toxicity problems associated with potential therapeutic chemicals may also be identified, as *C. elegans*, like humans, is a eukaryotic organism.

In yet another embodiment of the invention, manipulations can also be made to the nematode side of the *C. elegans* infection system because of the genetic tractability of *C. elegans*, i.e., ability to genetically manipulate this model organism. Even though *C. elegans* shares many protein homologues with humans, some receptors present on human cells to which bacterial antigens bind may be absent from the cells of the nematode. The desired human receptors can be expressed in nematodes in order to exploit specific microbe-host interactions for screening disrupting chemical agents. Because chemicals present in a liquid medium are taken into the nematode gut via pharyngeal pumping, our infection system can also be used for identifying chemical agents that disrupt viral pathogen adsorption to specific human receptor molecules.

The in vivo systems described herein include a model for use with the causative agent of traveler's diarrhea, also a common cause of childhood diarrhea in developing countries, enterotoxigenic *E. coli* (ETEC). There is a great need to develop effective, inexpensive therapies against ETEC to protect travelers visiting the developing world against this bacterium and to reduce its morbidity and mortality burden on children. ETEC bacteria colonizes the nematode gut in statistically higher numbers than a laboratory control strain of *E. coli*, and the simple *C. elegans*/ETEC infection system can be used to screen, and thus develop chemical agents that disrupt ETEC infection.

Referring to FIG. 1, it was determined whether ETEC bacteria would be found in higher numbers within the nematode gut than the non-pathogenic, K-12 control strain MG1655. Age-synchronized L4 nematodes were placed on rifampin-containing NGM agar, a medium commonly used by researchers modeling bacterial infection in *C. elegans*, and CFA, a standard medium used to maximize expression of ETEC fimbriae, with pregrown lawns of rifampin-resistant bacteria as described previously. After 24 hours of incubation at 26° C. nematodes were harvested, washed, treated to kill bacteria external to the gut, pulverized and plated on selective media.

With continued reference to FIG. 1, on NGM agar (black graph bars) the ETEC strains H10407 and H10407P lacking a virulence plasmid were found at a mean of ~$1 \times 10^4$ CFU per nematode and the number of MG1655 CFU per nematode was <10, a difference of at least three orders of magnitude. In contrast, on CFA medium (gray graph bars) H10407 and H10407P bacteria were found at a mean of ~$3 \times 10^4$ CFU per nematode, whereas the mean for control strain MG1655 was ~$4 \times 10^3$ CFU per nematode, a difference of approximately one order of magnitude. The difference between the ETEC strains H10407 and H10407P, and control MG1655 in their ability to colonize the nematode gut was statistically significant on both NGM and CFA media (NGM: $P<0.001$; CFA: $P=0.006$).

There was no significant difference in CFU per nematode values for wild type (wt) H10407 and the virulence plasmid lacking strain H10407P on either NGM or CFA agar. Because the H10407 and H10407P strains were able to colonize the nematode gut similarly, it may be concluded that factors in addition to the CFA/I fimbria, the CfaR regulator, or the ST toxin encoded on the H10407 virulence plasmid contributed to this phenotype.

Figures 2A, 2B, 2C, 2D, 2E, 2F, 2G, 2H, 2I, 2J, 2K, 2L:
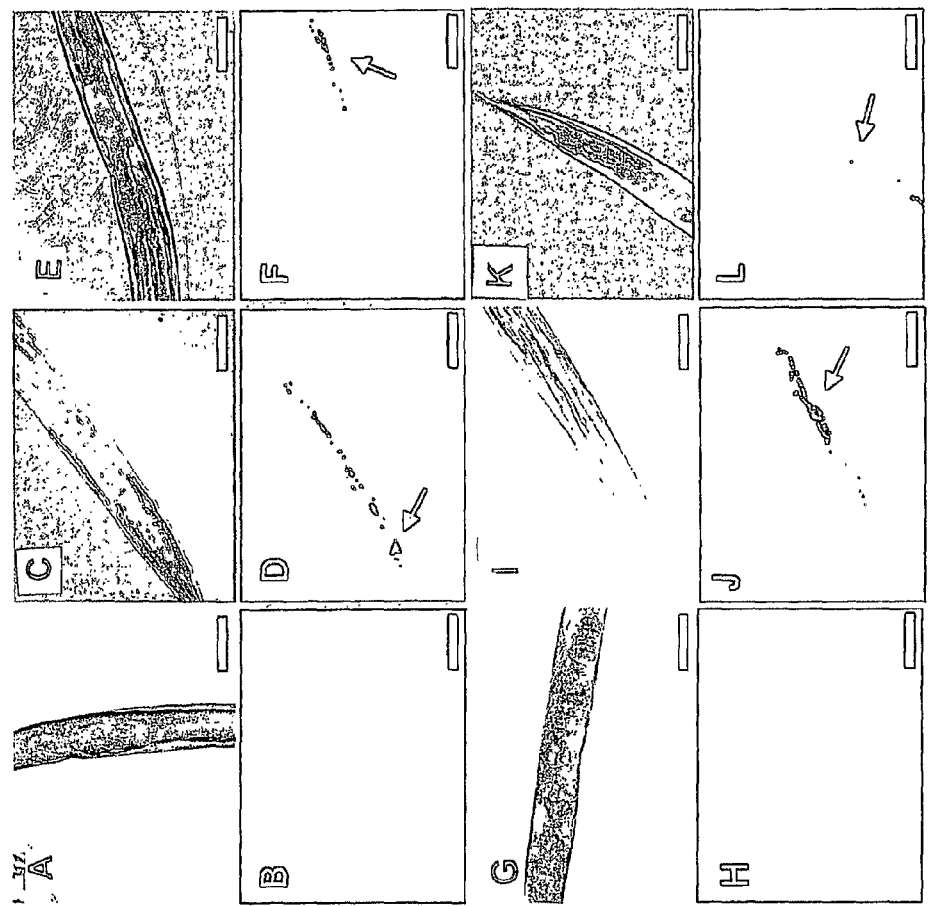
FIGS. 2A-2L comprise fluorescence microscopy images of ETEC bacteria within a nematode gut. After synchronization, LA nematodes were subjected to infection by ETEC and control strain MG1655 containing the GFP-producing plasmid pKH91 on NGM agar or CFA supplemented with appropriate antibiotics. After 24 hours, bacterial strains MG1655 (NGM: A, B; CFA: G, H), H10407 (NGM: C, D; CFA: I, J), and H10407P (NGM: E, F; CFA: K, L) were viewed by fluorescence and light microscopy. Light microscopy images (A, C, E, G, I, K) appear adjacent to fluorescent microscopy images (B, D, F, H, J, L). Arrows point to fluorescent bacteria. Representative images are presented. Magnification, ×200. Bars, 100 μm.

Referring to FIGS. 2A-2L, the ability of ETEC bacteria to colonize the nematode gut by fluorescence microscopy was observed. Consistent with values obtained by standard plate count assays, GFP-labeled wt H10407 bacteria 24 hours post-infection were observed on both NGM and CFA and (FIGS. 2D and 2J, respectively). In contrast to ETEC strain H10407, there was no colonization of the nematode gut by the control strain MG1655 on either NGM or CFA agar (FIGS. 2B and 2H). GFP-labeled ETEC strain H10407P were propagated on NGM and CFA within the nematode gut and observed by fluorescence microscopy (FIGS. 2F and 2L), but not as consistently as for the wt strain H10407 (FIGS. 2D and 2J).

Figure 3:
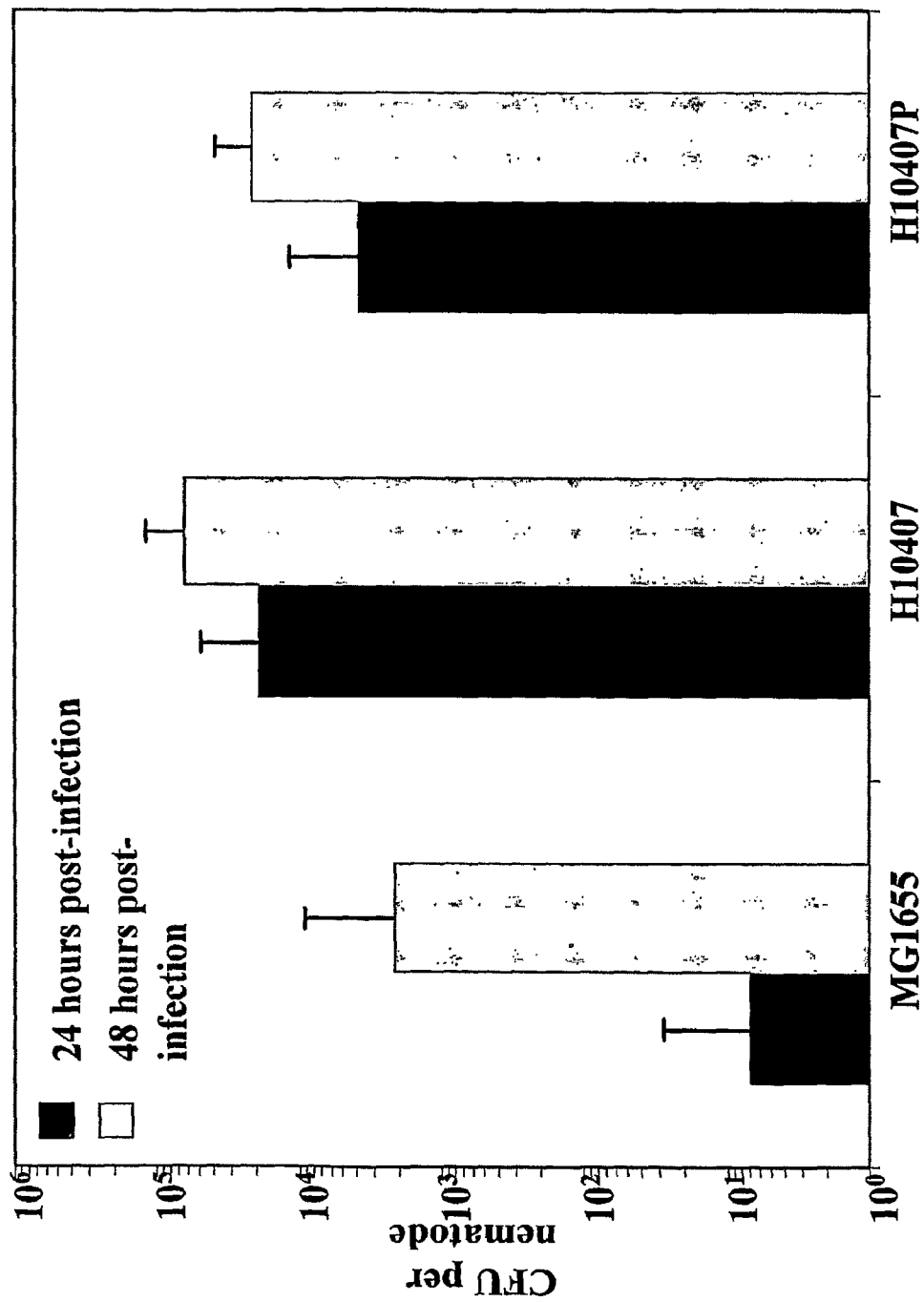
FIG. 3 is a graph demonstrating persistence of ETEC, showing the average CFU per nematode infected with the indicated bacterial strains on NGM agar. Twenty-four hours post-infection nematodes were transferred to rifampin sensitive MG1655 and harvested after 24 hrs (black bars) and 48 hrs (gray bars) of feeding. Values represent the means of three replicate assays, and error bars indicate 1 SD.

As shown in FIG. 3, prior to assessing feasibility of using the *C. elegans* model to screen for potential chemotherapeutic agents, it was investigated whether ETEC bacteria persist within the nematode gut. Nematodes were infected with rifampin-resistant ETEC or control bacteria. After 24 hours at 26° C. they were washed and placed on non-selective media containing the rifampin-sensitive strain MG1655. Twenty-four and 48 hours after the shift, the standard plate count assay was performed as described herein. At the 24-hour time point, rifampin-resistant strains H10407 and H10407P were found to be $2 \times 10^4$ and $5 \times 10^3$ CFU per nematode, respectively, whereas CFU per nematode for strain MG1655 was <10 CFU per nematode. Comparison of recoverable ETEC CPU per nematode versus that of MG1655 was significant (H10407: $P<0.001$; H10407P: $P<0.001$) (FIG. 3). At the 48-hour point, all strains tested showed increased numbers within the nematode gut compared to the 24-hour time point and the values were: $5 \times 10^4$, $2 \times 10^4$ and $2 \times 10^3$ for strains H10407, H10407P and MG1655, respectively. Again, the values for strain H10407 and H10407P were significantly different than that of strain MG1655 ($P=0.001$; $P=0.025$, respectively). As shown by FIG. 3, ETEC bacteria persist within the nematode gut at least 48 hours after shift onto NGM agar containing a non-pathogenic, laboratory strain of *E. coli*.

In one embodiment, a *C. elegans*/ETEC infection system can be used to screen for chemotherapeutic agents able to disrupt colonization of the nematode gut. In another embodiment, a *C. elegans*/ETEC infection system may be used to test a range of compounds including, for purposes of example only, the bacteriocidal antibiotic gentamicin, bacteriostatic antibiotic kanamycin, heparin, which may disrupt bacterial adherence, and mannose, which inhibits type I fimbria-mediated adherence to host cells. Age-synchronized L4 nematodes were placed on NGM agar inoculated with either strain H10407 or the control MG1655. Twenty-four hours post-infection, 30 nematodes fed each strain were placed in M9 buffer or M9 buffer supplemented with the desired compounds. After an additional 24 hours of incubation at 26° C., nematodes were harvested, washed to remove exterior bacteria, pulverized and plated on selective LB agar.

Figure 4:
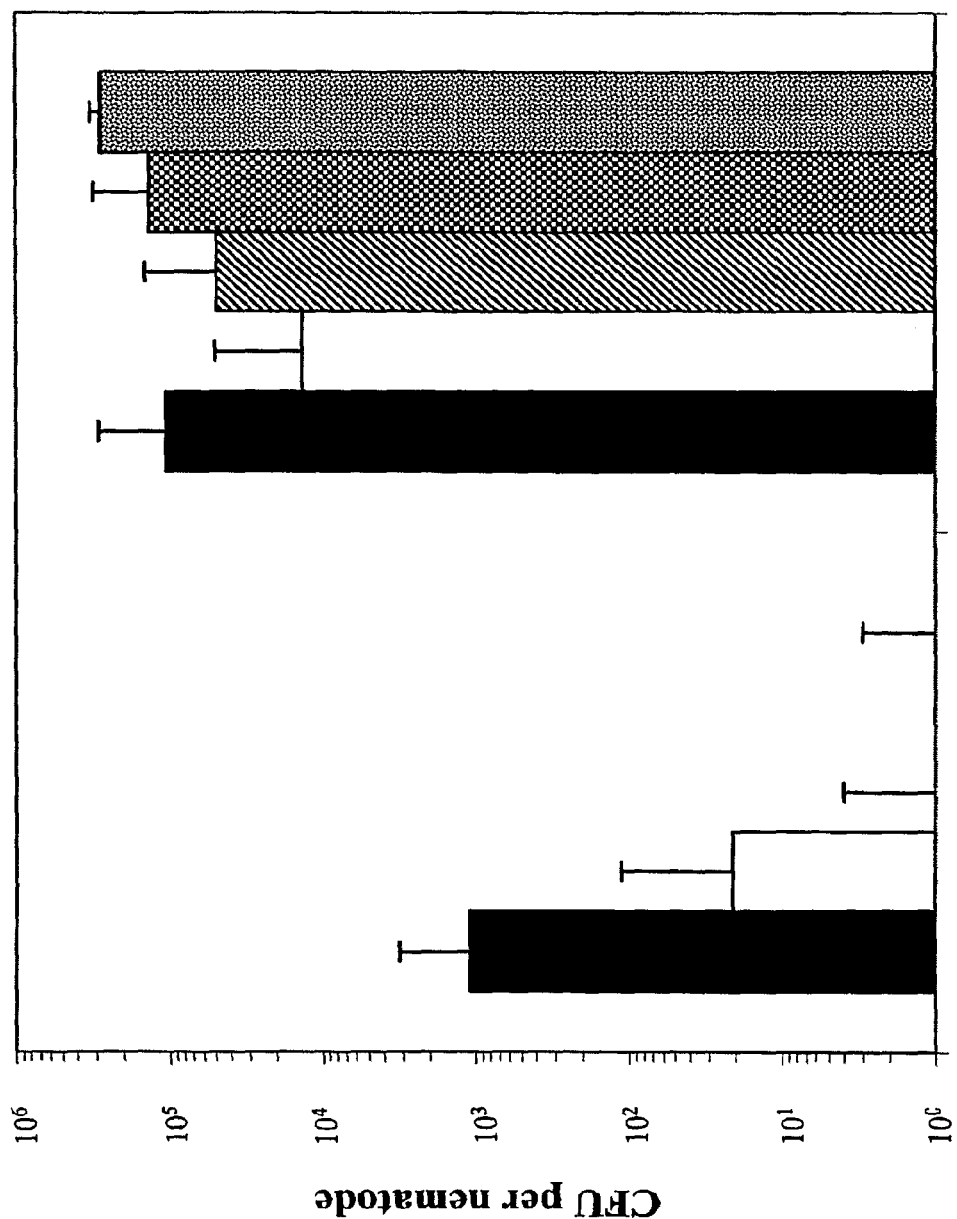
FIG. 4 is a graph demonstrating the effect of various compounds on bacterial colonization of the nematode gut. The graph shows the average CFU per nematode after they were exposed to the indicated rifampin-resistant bacteria strains. Nematodes were infected with prototypical ETEC H10407 or control MG1655 strains on NGM agar. After 24 hours of infection, 30 nematodes were harvested and placed in 1 mL M9 buffer (black bars), or M9 buffer supplemented with 100 μg/mL gentamicin (white bars), 50 μg/mL kanamycin (crosshatched bars), 7 μg/mL heparin (checkered bars), or 0.01% mannose (speckled bars), and incubated at 26° C. for 24 hours. Values represent the means of three replicate assays, and error bars indicate 1 SD.

As shown in FIG. 4, incubation of ETEC infected nematodes with gentamicin resulted in a significant (P=0.004) reduction in the number of bacteria recoverable from the nematode gut. The mean numbers of nematodes recoverable after incubation in M9 buffer versus M9 buffer supplemented with gentamicin were $1 \times 10^5$ and $1 \times 10^4$, respectively, approximately one order of magnitude. With continued reference to FIG. 4, there was no significant difference in the number of recoverable ETEC bacteria after treatment with any of the other compounds tested. Additionally, gentamicin reduced the number of enteropathogenic *E. coli* (EPEC) strain E2348/69 bacteria recoverable from the nematode gut by approximately one order of magnitude compared to those recovered from the untreated EPEC-infected nematodes (data not shown). In contrast, treatment of the control strain MG1655 with gentamicin, kanamycin, heparin and mannose resulted in significant reduction in the number of bacteria recovered from the nematode gut (P<0.001 for all compounds tested). The present invention therefore also includes a *C. elegans* small animal infection model for studying EPEC. Accordingly, a *C. elegans* infection system could be used to screen for potentially therapeutic chemical agents against multiple *E. coli* pathotypes.

Materials and Methods

Bacterial and Nematode Strains, Plasmids and Growth Media.

The bacterial and nematode strains, and plasmids used for this study are listed in Table 1. Spontaneous rifampin-resistant mutants of the *E. coli* strains were isolated to limit contamination and prevent growth of the *E. coli* feeding strain OP50 in colonization assays. *C. elegans* strain DH26 fer-15 (b26)II was obtained, which is sterile at 25° C. (*Caenorhabditis* Genetic Center) to ensure a constant number of nematodes during the assays due to their inability to reproduce when incubated at 26° C. Nematodes were propagated on pre-grown lawns of the *E. coli* food strain OP50 at 15° C. prior to synchronization for the assays described below.

TABLE 1

Bacterial and nematode strains, and plasmids.

| Strain or plasmid | Genotype or description |
|---|---|
| *E. coli* | |
| H10407 | wt ETEC serotype O78:H11 |
| H10407P | H10407 lacking the CFA/I-ST plasmid |
| MG1655 | F-λ- |
| OP50 | Uracil auxotrophy |
| *C. elegans* | |
| DH26 | fer-15(b26(II) Sterile at 25° C |
| Plasmids | |
| pKH91 | ori15A gfpuv bla Ap$^R$ tet Tc$^R$ |

Assays were performed on both nematode growth medium (NGM) agar (3 g NaCl, 2.5 g peptone, and 17 g agar to 1 liter in H$_2$O; after autoclaving, add 1 ml 1 M CaCl$_2$, 1 ml 1M MgSO$_4$, 1 ml 2-mg/ml uracil, 1 ml 5-mg/ml cholesterol in ethanol, and 25 ml 1 M KPO$_4$) and colonization factor agar (CFA) (10 g peptone, 1.5 g yeast extract, 0.05 g MgSO$_4$, 0.005 g MnCl$_2$, and 20 g agar in 1 liter H$_2$O) supplemented with the following antibiotics where appropriate: rifampin at 100 µg/ml and tetracycline at 15 µg/ml. NGM agar was supplemented with uracil because *E. coli* OP50 is a uracil auxotroph.

Standard Plate Count and Persistence Assays.

Prior to the assays, nematodes were age synchronized by a bleaching procedure. Briefly, nematodes/embryos grown on *E. coli* strain OP50 at 15° C. were harvested by washing the seeded NGM agar plate with M9 buffer (3 g KH$_2$PO$_4$, 6 g Na$_2$HPO$_4$, 5 g NaCl, 1 ml 1 M MgSO$_4$ in 1 liter H$_2$O), were placed into a microcentrifuge tube, and then washed three times with 1 ml M9 buffer after spinning for 10 seconds at 12,000 rpm. Nematodes/embryos were resuspended in 100 µM9 buffer and bleach treated by adding 350 µl 280 mM KOH and 50 µl bleach. Nematodes/embryos were agitated gently and mixed intermittently for 10 min. After a 10-second spin at 12,000 rpm, the supernatant was discarded, and embryos were washed twice more with 1 ml M9 buffer as described above. After a final spin, the embryos and dead nematodes were resuspended in 50 µl M9 buffer; the suspension was placed on NGM agar plates with the food strain OP50, without antibiotic selection, and incubated at 26° C.

After 3 days at 26° C., L4 nematodes were removed from feeding using a platinum wire and placed on rifampin-containing NGM agar plates with pre-grown ETEC and control strains that were incubated at 37° C. overnight. Prior to seeding of *C. elegans*, NGM and CFA agar plates were shifted to 26° C., the temperature where they remained for the duration of the assay. For the standard plate count assay, nematodes were fed on ETEC and control strains for 24 hours. Ten nematodes were then chilled in M9 buffer for 24 hours at 4° C. to loosen bacteria adherent to the nematode cuticle, washed three times in M9 buffer, treated with 100 µg/ml gentamicin at 37° C. for 1 hour to kill exterior bacteria, again washed three times with M9 buffer, treated with 50% chloroform saturated M9 buffer for 10 minutes, washed three times in M9 buffer containing 1% saponin and 1% Triton X-100, pulverized for 10 seconds using a sterile plastic pestle and a Ryobi hand-held cordless drill, and finally plated on LB agar containing rifampin.

For the persistence assay, nematodes were fed on rifampin-resistant ETEC and control strains for 24 h at 26° C., washed thrice with M9 buffer, then transferred to pre-grown lawns of non-resistant MG1655 for 24 h at 26° C. Subsequently, nematodes were harvested and treated as described in the standard plate count assay above. Standard plate count, and persistence data did not fit a Poisson model due to over dispersion, and thus were analyzed by negative binomial regression using Stata, version 7.0 (Stat Corp., College Station, Tex.).

Fluorescence Microscopy.

Synchronized L4 nematodes were subjected to infection by ETEC and MG1655 strains containing the green fluorescent protein (GFP)-producing plasmid pKH91 on NGM and CFA supplemented with rifampin and tetracycline at 26° C. Twenty-four hours after infection, nematodes were removed using a platinum wire and placed in 500 µl of M9 buffer. Immediately prior to microscopy, 500 µl of a saturated solution of chloroform in M9 buffer was added to the nematodes, and they were incubated at room temperature for 10 minutes to kill and remove any bacteria adherent to the exterior. Nematodes were washed six times in 1 ml M9 buffer, chilled, transferred to 1% agarose pads on glass microscope slides to control the rate of desiccation, and visualized using an Olympus BX60 microscope fitted with an Optronics Microfire digital camera (Optronics, Goleta, Calif.).

Screen to Evaluate Chemotherapeutic Agents Against ETEC Infection.

Age-synchronized nematodes were placed on rifampin-containing NGM agar plates with pre-grown ETEC or MG1655 strains that were previously incubated at 37° C. overnight. (Prior to seeding with *C. elegans*, NGM agar plates were shifted to 26° C.). Nematodes were infected with the *E. coli* by feeding them on ETEC and control strains for 24 h, after which ten nematodes were transferred into a microcentrifuge tube for treatment with 1 ml M9 buffer containing either gentamicin (100 µg/ml), kanamycin (50 µg/ml), heparin (7.14 mg/ml), β-defensin at 10 µg/ml, or mannose at 0.01%, or no additional compound as a negative control for 24 h at 26° C. After treatment the nematodes were washed with M9 buffer to remove the treatment compound, chilled on ice at 4° C. overnight to loosen bacteria adherent to the cuticle, and washed as described for the standard plate count and persistence assays described above.

While specific embodiments and applications of infection models have been illustrated and described, it is to be understood that the invention claimed hereinafter is not limited to the precise methods, configurations, and components disclosed. Various modifications, changes, and variations apparent to those of skill in the art may be made in the arrangement, operation, and details of the methods, devices, and systems disclosed.

References

1. Alegado, R. A., M. C. Campbell, W. C. Chen, S. S. Slutz, and M. W. Tan. 2003. Characterization of mediators of microbial virulence and innate immunity using the *Caenorhabditis elegans* host-pathogen model. Cell Microbiol 5:435-44.
2. Barrett, J. F. 2005. Can biotech deliver new antibiotics? Curr Opin Microbiol 8:498-503.
3. Blattner, F. R., G. Plunkett, 3rd, C. A. Bloch, N. T. Perna, V. Burland, M. Riley, J. Collado-Vides, J. D. Glasner, C. K. Rode, G. F. Mayhew, J. Gregor, N. W. Davis, H. A. Kirkpatrick, M. A. Goeden, D. J. Rose, B. Mau, and Y. Shao. 1997. The complete genome sequence of *Escherichia coli* K-12. Science 277:1453-74.
4. Brenner, S. 1974. The genetics of *Caenorhabditis elegans*. Genetics 77:71-94.
5. Dowell, S. F. 2004. Antimicrobial resistance: is it really that bad? Semin Pediatr Infect Dis 15:99-104.
6. Evans, D. G., D. J. Evans, Jr., and W. Tjoa. 1977. Hemagglutination of human group A erythrocytes by enterotoxigenic *Escherichia coli* isolated from adults with diarrhea: correlation with colonization factor. Infect Immun 18:330-7.
7. Evans, D. G., D. Y. Graham, and D. J. Evans, Jr. 1984. Administration of purified colonization factor antigens (CFA/I, CFA/II) of enterotoxigenic *Escherichia coli* to volunteers. Response to challenge with virulent enterotoxigenic *Escherichia coli*. Gastroenterology 87:934-40.
8. Evans, D. G., R. P. Silver, D. J. Evans, Jr., D. G. Chase, and S. L. Gorbach. 1975. Plasmid-controlled colonization factor associated with virulence in *Escherichia coli* enterotoxigenic for humans. Infect Immun 12:656-67.
9. Evans, D. J., Jr., and D. G. Evans. 1973. Three characteristics associated with enterotoxigenic *Escherichia coli* isolated from man. Infect Immun 8:322-8.
10. Galen, J. E., J. Nair, J. Y. Wang, S. S. Wasserman, M. K. Tanner, M. B. Sztein, and M. M. Levine. 1999. Optimization of plasmid maintenance in the attenuated live vector vaccine strain *Salmonella typhi* CVD 908-htrA. Infect Immun 67:6424-33.
11. Gauthier, A., M. L. Robertson, M. Lowden, J. A. Ibarra, J. L. Puente, and B. B. Finlay. 2005. Transcriptional inhibitor of virulence factors in enteropathogenic *Escherichia coli*. Antimicrob Agents Chemother 49:4101-9.
12. Hung, D. T., E. A. Shakhnovich, E. Pierson, and J. J. Mekalanos. 2005. Small-molecule inhibitor of *Vibrio cholerae* virulence and intestinal colonization. Science 310:670-4.
13. Iredell, J., and J. Lipman. 2005. Antibiotic resistance in the intensive care unit: a primer in bacteriology. Anaesth Intensive Care 33:188-95.
14. Kim, D. H., R. Feinbaum, G. Alloing, F. E. Emerson, D. A. Garsin, H. Inoue, M. Tanaka-Hino, N. Hisamoto, K. Matsumoto, M. W. Tan, and F. M. Ausubel. 2002. A conserved p38 MAP kinase pathway in *Caenorhabditis elegans* innate immunity. Science 297:623-6.
15. Knutton, S., J. Adu-Bobie, C. Bain, A. D. Phillips, G. Dougan, and G. Frankel. 1997. Down regulation of intimin expression during attaching and effacing enteropathogenic *Escherichia coli* adhesion. Infect Immun 65:1644-52.
16. Laws, T. R., S. A. Smith, M. P. Smith, S. V. Harding, T. P. Atkins, and R. W. Titball. 2005. The nematode *Panagrellus redivivus* is susceptible to killing by human pathogens at 37 degrees C. FEMS Microbiol Lett 250:77-83.
17. Livermore, D. M. 2004. The need for new antibiotics. Clin Microbiol Infect 10 Suppl 4:1-9.
18. Mellies, J. L., A. M. Barron, K. R. Haack, A. S. Korson, and D. A. Oldridge. 2006. The global regulator Ler is necessary for enteropathogenic *Escherichia coli* colonization of *Caenorhabditis elegans*. Infect Immun 74:64-72.
19. Nataro, J. P., and J. B. Kaper. 1998. Diarrheagenic *Escherichia coli*. Clin Microbiol Rev 11:142-201.
20. Nguyen, T. V., P. V. Le, C. H. Le, and A. Weintraub. 2005. Antibiotic resistance in diarrheagenic *Escherichia coli* and *Shigella* strains isolated from children in Hanoi, Vietnam. Antimicrob Agents Chemother 49:816-9.
21. Ogiernan, M. A., A. W. Paton, and J. C. Paton. 2000. Up-regulation of both intimin and eae-independent adherence of shiga toxigenic *Escherichia coli* O157 by ler and phenotypic impact of a naturally occurring ler mutation. Infect Immun 68:5344-53.
22. Parry, C. M. 1998. Untreatable infections?—The challenge of the 21st century. Southeast Asian J Trop Med Public Health 29:416-24.
23. Roberts, T. M., and S. Ward. 1982. Membrane flow during nematode spermiogenesis. J Cell Biol 92:113-20.
24. Salyers, A. A., and Whitt, Dixie D. 2005. The looming crisis of antibiotic availability, p. 116-129, in Revenge of the Microbes: how bacterial resistance is undermining the antibiotic miracle. ASM Press, Washington D.C.
25. Sifri, C. D., J. Begun, F. M. Ausubel, and S. B. Calderwood. 2003. *Caenorhabditis elegans* as a model host for *Staphylococcus aureus* pathogenesis. Infect Immun 71:2208-17.
26. Thomas, R., and T. Brooks. 2004. Common oligosaccharide moieties inhibit the adherence of typical and atypical respiratory pathogens. J Med Microbiol 53:833-40.
27. Ulrich, R. L. 2004. Quorum quenching: enzymatic disruption of N-acylhomoserine lactone-mediated bacterial communication in *Burkholderia thailandensis*. Appl Environ Microbiol 70:6173-80.

The invention claimed is:
1. A *C. elegans* infection method for testing the effect of a compound on an organism, the method comprising:

infecting at least one strain of *C. elegans* with the organism;

dividing the infected *C. elegans* into a treatment group and a control group;

treating the infected *C. elegans* in the treatment group with at least one desired compound; and measuring the effect of the compound on the organism,
wherein measuring the effect of the compound on the organism comprises:

pulverizing the infected *C. elegans* from the treatment group and pulverizing the infected *C. elegans* from the control group;

culturing the pulverized infected *C. elegans* from the treatment group and culturing the pulverized infected *C. elegans* from the control group; and comparing the number of cultured organisms from the pulverized infected *C. elegans* treatment group to the number of cultured organisms from the pulverized infected *C. elegans* control group, wherein a lesser number of cultured organisms from the pulverized infected *C. elegans* treatment group compared to the number of cultured organisms from the pulverized infected *C. elegans* control group indicates the compound has a negative effect on the organism.

2. The method of claim 1, wherein the strain of *C. elegans* is infected with a bacterial pathogen.

3. The method of claim 2, wherein the bacterial pathogen is an enteric bacterial pathogen.

4. The method of claim 3, wherein the enteric bacterial pathogen comprises at least one enteric bacteria selected from the group consisting of *Salmonella* spp., *Campylobacter* spp., *E. coli*, *Shigella* spp., *Helicobacter pylori*, *Vibrio* spp., *Clostridium* spp., and combinations thereof.

5. The method of claim 1, wherein the compound is an anti-infective compound configured to block or disrupt or both block and disrupt pathogen-host interactions.

6. The method of claim 1, wherein the compound is an antibiotic.

7. The method of claim 1, wherein the compound is a chemotherapeutic to combat diarrheal disease caused by *E. coli* bacteria.

8. The method of claim 1, wherein the compound is selected from the group consisting of gentamicin, kanamycin, heparin, β-defensin, mannose, and combinations thereof.

9. The method of claim 1, wherein the compound is an agent configured to disrupt the colonization of *C. elegans* by the organism.

10. The method of claim 1, wherein the organism is a bacterial pathogen comprising a green fluorescent protein (GFP).

11. The method of claim 10, wherein comparing the number of cultured organisms from the pulverized infected *C. elegans* treatment group to the number of cultured organisms from the pulverized infected *C. elegans* control group comprises comparing the number of cultured GFP-expressing bacterial pathogen from the pulverized infected *C. elegans* treatment group to the number of cultured GFP-expressing bacterial pathogen from the pulverized infected *C. elegans* control group with fluorescence microscopy.

* * * * *